Figure 1:
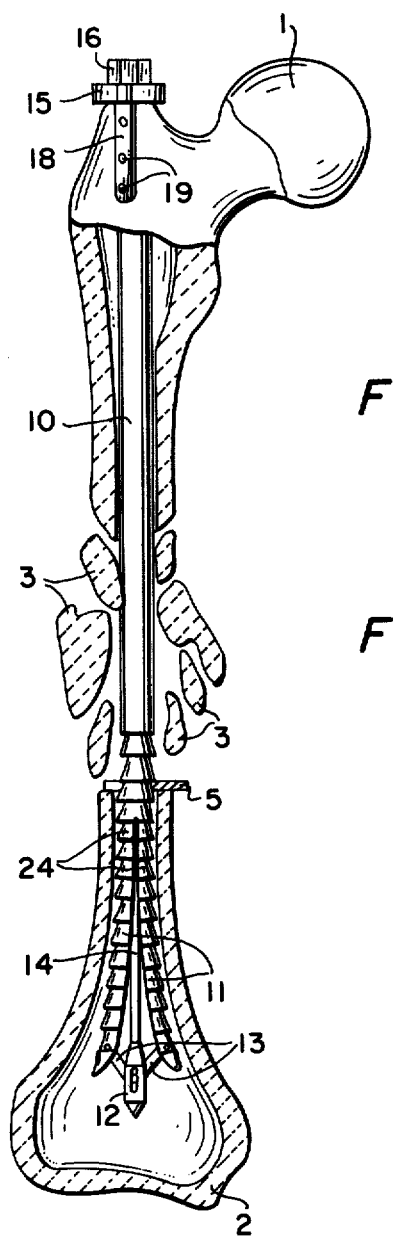

United States Patent [19]

Aginsky

[11] 4,227,518
[45] Oct. 14, 1980

[54] INTRAMEDULLARY RETRACTION NAIL FOR FIXATION OF COMMINUTED FRACTURED BONES

[76] Inventor: Jacob Aginsky, 18 Rachel St., Haifa, Israel

[21] Appl. No.: 5,890

[22] Filed: Jan. 23, 1979

[30] Foreign Application Priority Data

Feb. 12, 1978 [IL] Israel ................................. 54022

[51] Int. Cl.³ .................... A61B 17/18; A61F 5/04
[52] U.S. Cl. .......................... 128/92 BC; 128/92 D
[58] Field of Search ............ 128/92 BC, 92 R, 92 B, 128/92 BA, 92 D

[56] References Cited

U.S. PATENT DOCUMENTS

| 3,759,257 | 9/1973 | Fisher et al. | 128/92 BC |
| 3,805,775 | 4/1974 | Fisher et al. | 128/92 BB |

FOREIGN PATENT DOCUMENTS

| 2030249 | 12/1971 | Fed. Rep. of Germany | 128/92 BB |
| 2701279 | 7/1977 | Fed. Rep. of Germany | 128/92 BC |
| 587915 | 1/1959 | Italy | 128/92 BA |

*Primary Examiner*—Ronald L. Frinks
*Attorney, Agent, or Firm*—Schwartz, Jeffery, Schwaab, Mack, Blumenthal & Koch

[57] ABSTRACT

An intramedullary retraction nail serves to keep the two ends of a fractured and splintered bone at the correct distance and in correct alignment. For this purpose the nail is provided with an expansion element at its front end which can be expanded so as to grip the inside of the cavity walls of one bone end. The expansion of this element is carried out by manipulation of an expanding mechanism from the rear end of the nail protruding out of the other end of the bone. This bone end is held in position by one or two connector strips fastened thereto by screws, while the rear ends of these strips are attached to a retractor body which can be moved along the threaded end of the intramedullary nail so as to stretch the bone parts to their original distance. The retractor body is prevented from rotating about the nail end, thus the fractured bone parts are not only held at their correct distance but also in a desired angular alignment.

10 Claims, 9 Drawing Figures

U.S. Patent    Oct. 14, 1980    Sheet 1 of 2    4,227,518

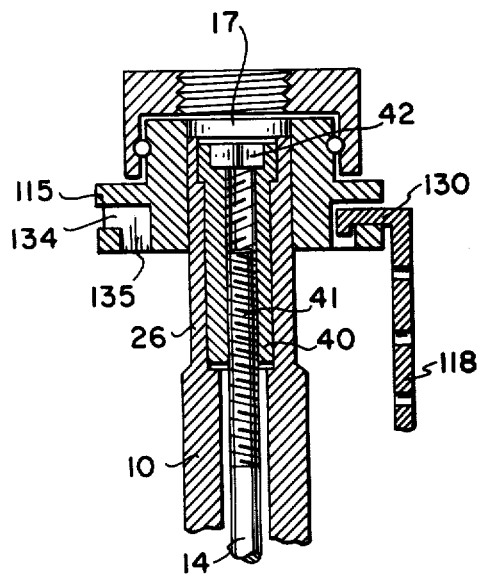
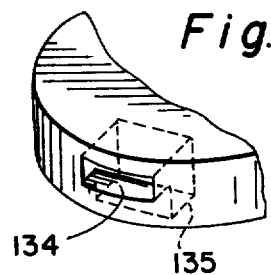
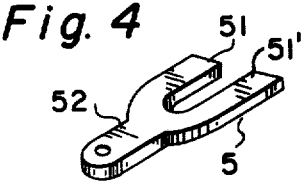
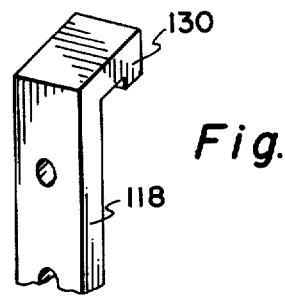

INTRAMEDULLARY RETRACTION NAIL FOR FIXATION OF COMMINUTED FRACTURED BONES

The invention relates to a supporting device for a comminutely fractured tubular bone, instrumental in keeping the bone fragments aligned by its insertion into the medullary cavity of the bone, until the bone structure has healed to its original size and strength.

Intramedullary nails are known for treatment of bone fractures, particularly for so-called simple fractures whereby the bone has suffered one—or maximum two—fractures which can be cleanly fitted together again. In these cases a so-called "compression-nail" can be used that is characterised by that its leading end—which is inserted into the cavity head first—is expandable,—and that its trailing end—which protrudes out of the bone end—is provided with axial compression means. This kind of compression nail is driven into the fractured bone until the leading end has reached the flared-out end portion of the medullary cavity wherein it is expanded and pressed against the cavity walls. The trailing end of this kind of nail is generally provided with outer screw threads on which a compression disc can be pressed against the bone end by the tightening of a nut, whereby the bone fragments are compressed at their fractured ends and immobilized against relative movement. In my Israeli Pat. Spec. No. 48826 or U.S. counterpart, U.S. Pat. No. 4,091,806 I have described a compression nail of this kind which, however, has been improved by me by incorporating the important feature of having the expanding and the compressing operations made completely independent from each other, i.e. the expansion at the leading end can be wholly completed before the compression starts by the tightening of the aforementioned nut. A second feature of the above improved nail is the prevention of the nail's angular rotation in the bone cavity by providing the outer sheath of the device with flat portions and by providing a compression disc with a central hole of similar, corresponding proportions and with two prongs that can be pressed into the bone material; since the compression ring is thus firmly anchored in the bone, it likewise prevents angular movement of the compression nail.

With comminuted fractures, particularly where the middle portion of the bone is splintered into several parts, this kind of nail is unsuitable, since there exist no clean fractured surfaces which can be pressed against each other. To heal these fractures it is customary to insert a nail and to stretch the limb by weights or like apparatus, in the hope that the bone fragments will join and heal to the original shape and length of the bone. Another way of keeping the bone ends at the previous distance is by driving transverse nails or screws through the bone and through holes in an intramedullary nail inserted therein in order to prevent the bone from being shortened by muscle contraction.

These methods are rather coarse and their use frequently leads to a shortened limb, in addition to keeping the patient immobilized with known consequences to follow.

Still another method of keeping the end fragments at a fixed distance comprises driving nails transversely through the bone and through the fleshy parts and connecting the nail ends on the outside by perforated rigid strips, the so-called Hoffman Fixators. This method, in addition to immobilizing the patient for a lengthy period, often leads to infections by impurities entering along the nails.

It is therefore the object of the present invention to provide an intramedullary nail adapted to be inserted into a fractured and splintered tubular bone and permitting the surgeon to adjust the distance of the outer fragments to the original bone length, so as to make it possible for the splintered fragments to join and to grow bone material in the fractures, with the ultimate result of obtaining a healed bone of the original size and length.

The intramedullary retraction nail, according to the invention, comprises an outer tubular sheath, its leading or front end being shaped to form at least two expandable branches which are adapted to be spread and pressed against the bone cavity walls by expanding means of a kind known to the art. The front portion of the sheath, including the branches, is provided with circumferential serrations in saw shape, each serration decreasing in diameter from its front to its rear. The retraction nail further comprises a longitudinal bar movable inside the tubular sheath and adapted to actuate the said expanding means by being manually operated from the trailing or rear end of the nail which latter protrudes by a short length out of the previously perforated bone end. The rear portion of the sheath is cylindrical except for at least one flat longitudinally extending surface, and is provided with outer screw thread which is interrupted by the said flat surface. An annular retraction body axially movable on the sheath end consists of a centrally perforated disc and an internally threaded nut, the disc and the nut being interconnected in a manner permitting their relative rotation about their common axis, but not their relative axial movement, the disc being prevented from rotating about the threaded sheath portion by being provided with a central perforation in the shape of the flattened profile of the sheath. The perforated disc is further provided with means for hingedly attaching to it one or more perforated flat connector strips adapted to be connected to the bone sides by nails or screws. The retractor body, together with the attached connector strips can be forcefully moved along the threaded sheath portion by manual rotation of the nut.

The retraction nail is used in the following way to fasten the fractured bone parts:

Into the rear end of the bone a hole is drilled of a diameter permitting the insertion of the non-expanded nail into the intrammedullary cavity of the rear fragment and from there into the suitably aligned cavity of the front fragment, the splintered parts not being aligned at this stage.

By manipulating the longitudinal bar the expandable sheath branches are pressed against the cavity walls, a torque wrench being used for this operation to ensure a firm grip of the nail in the flared-out cavity without, however, destroying the bone structure. Now the retracting body is moved along the sheath in a forward direction by rotating the nut until it meets the rear end of the bone, two perforated connecting strips are fastened to the body in approximately opposite points, extending alongthe bone surface, and are attached to the bone by nails or screws. At the same time a thin U-shaped retainer is slipped sideways into a serration nearest the fracture of the frontal bone fragment, thus preventing longitudinal shifting of the nail in this bone portion. The two bone ends are now pulled apart to the distance they had before the fracture occurred, by rotating the nut rearwardly on the threaded sheath end thereby moving the retractor body together with the rear bone fragment attached thereto away from the front end of the bone. The separate bone splinters are now arranged around the nail between the end portion more or less in their original order and the wound is now closed.

After 4 to 6 months, when the several bone fragments have jointed to a firm structure, the above U-shaped retainer is removed by pulling it sideways out of the serration, and the intramedullary nail is now used as a compression nail in a known manner, by tightening said nut and the retracting body against the rear bone end, thereby compressing the fractured parts together. After a further period when the bone has completely healed, the nail is extracted by first reclosing the expanded branches, removing the nails or screws which had attached the connector strips to the bone sides, and then knocking the nail out of the cavity in a manner known to the art. Healing of the fleshy parts is then a matter of a few days.

Figure 2:
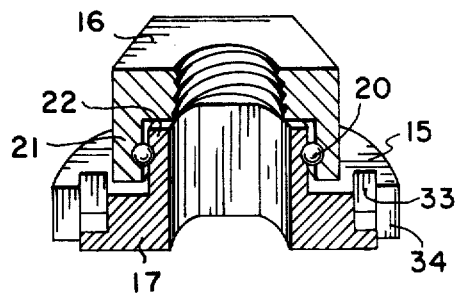
Figure 3:
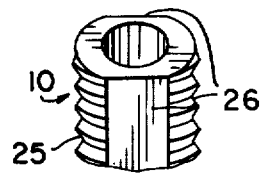
Figure 5:
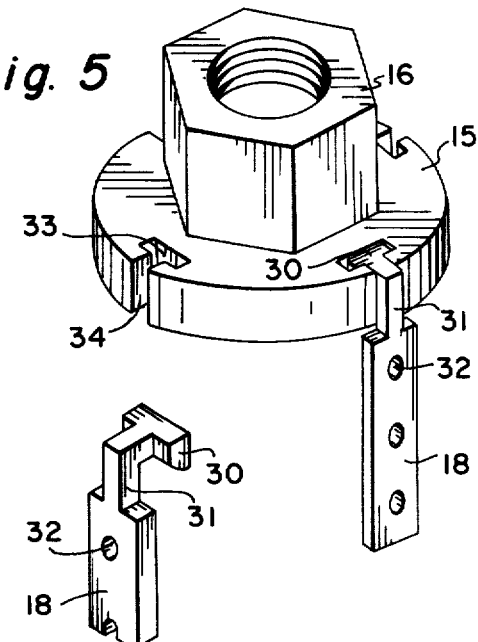
Figure 6:
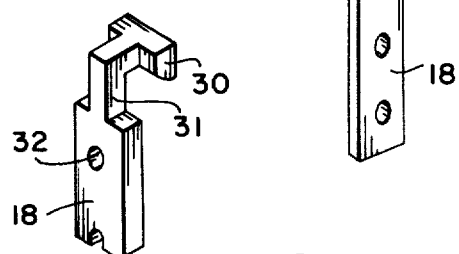

In the accompanying drawings which illustrate, by way of example, two embodiments of the invention, FIG. 1 is a general view of an intramedullary retraction nail embedded in a fractured thigh bone, FIG. 2 is a section through a retractor body, FIG. 3 is a view of the rear end of a tubular sheath, FIG. 4 is a view of a U-shaped retainer piece, FIG. 5 is a view of a retractor body showing one connector strip attached thereto, FIG. 6 is a view of the upper part of a connector strip, before its attachment to the retractor body, FIG. 7 is a longitudinal section through the rear portion of the retraction nail as illustrated in FIG. 1, showing another embodiment of the connector strip and its attachment to the retractor body, FIG. 8 is a detail of the aperture in the retractor body of FIG. 7 for inserting therein a connector strip, and FIG. 9 is a view of another embodiment of the connector strip to be inserted into the aperture as shown in FIG. 8.

With reference to the drawings, FIG. 1 shows a fractured thigh-bone comprising a top or rear fragment 1, a bottom or front fragment 2 and a number of unconnected splinters 3. The Figure further shows a retraction nail according to the invention, inserted into the intramedullary cavity of the two bone ends, the insertion being through a hole previously drilled into the rear end of fragment 1. The nail comprises a tubular sheath 10 the front end of which is split into two spreadable branches 11 adapted to be expanded against the cavity walls by an expandor body 12 and two links 13 which are, at their respective ends, hingedly connected to the expander body 12 and to each of the branches 11. The body 12 is pulled rearwards by a longitudinal bar 14 whereby the links open up out of their original position and spread the branches.

A mechanism of this kind is the subject matter of my Israeli Pat. Spec. No. 53703 and U.S. counterpart, U.S. Application Ser. No. 970,830, filed Dec. 19, 1978, but it is understood that any other method of expanding the front end of the nail as known to the art, may be used, such as, for instance a wedge drawn rearwards between the originally adjacent branches which pushes these apart; this kind of expander has, inter alia, been described in my Israeli Pat. Spec. No. 48826 or U.S. Pat. No. 4,091,806.

The front end of the tubular sheath, including the branches 11, is provided with saw-shaped, circumferential serrations 24, each such serration decreasing in diameter from the front to the rear from a maximum to a minimum value; they serve to secure the nail in the cavity of the frontal fragment as will be described hereinafter.

As shown in FIG. 3, the rear end of the sheath is provided with outer screw thread 25 interrupted along its entire length by two longitudinally extending flat surfaces 26 on opposite sides of the sheath. A retractor body, as shown in FIG. 2, consists of a centrally perforated disc 15 and an internally threaded nut 16 rotatably connected thereto; the body can be moved forward and rearward along the sheath by turning the nut 16 on the thread 25, the disc 15 being prevented from rotating about the sheath by virtue of the shape of its central perforation which corresponds to the cross section of the rear portion of the sheath, i.e. it is provided with two internal flat surfaces 17 corresponding to the surfaces 26. Two connector strips 18 are pivotally attached to the disc 15 and are rigidily fastened to the bone sides by means of screws 19.

The disc 15 and nut 16 of the retractor body are connected to each other by balls of steel or plastic 20 inserted between an outer collar 21 of the nut and an inner collar 22 of the disc in corresponding circumferential grooves in said collars, which permit relative rotary movement, but not relative axial movement of the two components. By means of these balls it is possible to stretch the bone fragments apart by turning the nut on the screw thread 25, whereby the disc and the attached connector strips are pulled to the rear, while the bone front end is firmly held by the spread branches. The connector strips 18 can be attached to the retractor disc in four equidistant points; for this purpose the rear end of each connector strip 18 is shaped to form a hook 30 connected to the strip proper by a narrow neck portion 31. The strip is provided with three holes 32 serving to firmly connect the strip to the bone material by screws or nails 19. The retractor disc is provided in four places with rectangular recesses 33 open towards the rearward surface of the disc and communicating with the circumferential rim of the disc by slots 34 extending parallel to the disc axis across the entire disc width; the connector strip is inserted with its hook 30 into the recess 33, while the neck portion 31 rests in the slot 34; this allows a certain angular movement of the strip relative to the disc, both in outward and inward direction, to permit close attachment of the strip to the bone exterior.

Another kind of connection is shown in FIGS. 8 and 9: herein a connector strip 118 is of equal width throughout and is shaped to form a hook 130 at its rear end, likewise of the same width. This hook can be inserted into one of four apertures 134 provided in the disc circumference, each aperture being opened at its inner end to the disc surface by a recess 135. The inserted hook is illustrated in FIG. 7 which shows a section through the connector strip and the retractor disc 115. In addition FIG. 7 shows, in section, the rear portion of the retraction nail illustrated in FIG. 1, particularly the mechanism serving to pull the bar 14 to the rear for expanding the branches 11. The bar 14 is screw-threaded at its end which engages with the internal thread 41 of a sleeve 40 rotatably positioned in the rear end of the tubular sheath. The sleeve is provided in its rear end with a hexagonal recess for insertion of a hexagonal spanner. This kind of moving an internal bar or rod of an intramedullary nail is well known to the art and has been particularly described in the U.S. Pat. No. 3,759,257, Artur Fischer. In addition, FIG. 7 shows the detail of the position of the retractor body on the sheath 10.

FIG. 4 illustrates a U-shaped retainer piece 5 of small thickness, the distance between its two legs 51, 51' being slightly larger than the small diameter of the serrations 24. This permits its insertion into one of the serrations from one side, close to the fractured end of the front bone fragment 2, so as to prevent axial movement of the nail in the bone cavity. The retainer is provided at its end with a perforated flat handle 52 for easy insertion and withdrawal.

The main advantage of the aforedescribed retraction nail is that it enables the surgeon to adjust the distance between the fractured bone ends to an exact degree, and that the fractured ends are kept at the so-adjusted distance during the entire healing period. It is also understood that the bone fragments are prevented from rotating about the nail, since the front fragment is rigidly gripped by the expanded members, while the rear fragment is rigidly held between the connector strips. The retraction nail excels further in that its, use is not limited to retraction only, but that it is converted into a compression nail after partial healing and after withdrawal of the retainer piece.

The invention is not limited to the aforedescribed embodiments which are illustrated as examples only, but it is understood that various modifications may be carried out to the retraction nail, within the spirit of the invention by a person skilled in the art, and the following modifications are proposed, again as examples only:

One or two connector strips may be fastened to the retractor disc in preferably opposite positions; however, the disc may be modified so as to permit fastening of the strips at another angle than 180°, by providing elongated slots. It is not absolutely necessary to have four apertures in the disc, which are provided to permit attachment of two strips without wide angular adjustment of the disc together with the rest of the nail, but it may be sufficient to provide two apertures only.

The connection between the connector strips and the retractor disc may have any other suitable shape as long as it permits slight angular movement of the strips relative to the disc.

Instead of two opposed flat surfaces (26), only one side of the tubular sheath may be flattened, corresponding to the central perforation of the disc.

As mentioned hereinbefore, the frontal expansion portion may be of any kind used or described in previous publications, but it is my contention that the device shown in FIG. 1 of the drawing is the most suitable for the purpose of fixing a bone portion.

Instead of one retainer piece, two pieces may be inserted from different sides, so as to reinforce the connection between fractured end and the nail, and it is understood that the described shape of the retainer piece may be varied for different kinds of fractures.

Instead of the balls connecting the disc and the nut, any other anti-friction connection may be employed for this purpose, although the ball bearing has proved advantageous with regard to each manipulation of the retraction nail of the described kind.

I claim:

1. An intramedullary retraction nail comprising
   An outer sheath the leading or front end of which is
      shaped to form an expansion element of a kind known to the art adapted to be biased against the cavity walls of a fractured tubular bone by expanding means likewise known to the art positioned and movable inside the sheath and adapted to be operated from the protruding trailing or rear end of said sheath, the front portion of said sheath, including the expansion element, being provided with circumferential serrations in saw-shape, each serration decreasing in diameter from its front end to its rear end, the rear portion of said sheath being provided with outer screw thread interrupted by at least one flat, longitudinally extending surface,
   an annular retractor body axially movable on the rear sheath portion consisting of a centrally perforated disc and an internally threaded nut attached to the rear of said disc, said disc and said nut being interconnected in a manner permitting their relative rotation about their common axis, but not their relative axial movement, the disc being prevented from rotating about the threaded sheath portion by being provided with a central perforation corresponding to the shape of the flattened profile of the sheath rear portion,
   at least one perforated connector strip adapted to be attached to the bone side by means of screws or nails and provided with hook means adapted to hingedly engage with corresponding recesses in the disc of said retractor body, a U-shaped flat retaining piece comprising two legs spaced at a distance smaller than the largest diameter of each serration on said sheath, but larger than the smallest diameter of each serration.

2. An intramedullary retraction nail as defined in claim 1, wherein said annular retractor body comprises a threaded nut provided with an internal collar and the perforated disc is provided with an external collar positioned inside said external collar, and with a plurality of balls of steel or the like positioned in circumferential opposed grooves in said external and internal collars respectively, the collars and the balls forming together a ball bearing permitting relative rotary motion of the nut and the disc, but preventing their separation and relative axial motion of the two components of the retractor body.

3. An intramedullary retraction nail as defined in claim 1, comprising said tubular outer sheath rear portion provided with a screw thread being interrupted by two opposedly positioned flat surfaces.

4. An intramedullary retraction nail as defined in claim 1, comprising said at least one connector strip having a straight strip portion which is provided with a hook and a neck of narrower width than the straight strip portion, and with a hook end of a larger width than the hook and the neck.

5. An intramedullary retraction nail as defined in claim 4, comprising said retractor disc provided with at least one aperture for engaging with said hook and neck of the connector strip, this aperture consisting of a longitudinal rectangular recess in the rear surface of said disc communicating with the disc periphery by a slot extending across the entire thickness of the disc parallel to the nail axis.

6. An intramedullary retraction nail as defined in claim 5, comprising said retractor disc provided with four apertures adapted to engage with the hook portion of said connector strip, these apertures being equidistantly positioned on the periphery of said disc.

7. An intramedullary retraction nail as defined in claim 1, comprising said at least one connector strip consisting of a straight portion provided with screw holes and a hooked portion adapted to engage with an aperture in said retractor disc, the straight portion and the hooked portion being of the same width throughout.

8. An intramedullary retraction nail as defined in claim 7, comprising said retractor disc provided in its periphery with at least one aperture communicating with the front surface of the disc by means of a recess, serving to accommodate the hook portion of said connector strip.

9. An intramedullary retraction nail as defined in claim 8, comprising said retractor disc provided with four apertures adapted to engage with the hook portion of said connector strip, these apertures being equidistantly positioned on the periphery of said disc.

10. An intramedullary retraction nail as defined in claim 1, comprising in its front portion an expansion mechanism consisting of two expandable branches adapted to be spread by an axially movable expander body and two links hingedly connected at their ends to said expander body and to each of said branches.

* * * * *